US011152124B2

(12) United States Patent
Weir et al.

(10) Patent No.: US 11,152,124 B2
(45) Date of Patent: Oct. 19, 2021

(54) CONTACT TRACING SYSTEMS AND METHODS FOR TRACKING OF SHIPBOARD PATHOGEN TRANSMISSION

(71) Applicant: Royal Caribbean Cruises Ltd., Miami, FL (US)

(72) Inventors: Nicholas Weir, Davie, FL (US); Ernesto M. Rubi, Miramar, FL (US); Daniel John Altin, St Simons Island, GA (US)

(73) Assignee: ROYAL CARIBBEAN CRUISES LTD., Miami, FL (US)

(*) Notice: Subject to any disclaimer, the term of this patent is extended or adjusted under 35 U.S.C. 154(b) by 0 days.

(21) Appl. No.: 17/195,489

(22) Filed: Mar. 8, 2021

(65) Prior Publication Data
US 2021/0280321 A1 Sep. 9, 2021

Related U.S. Application Data (60) Provisional application No. 62/987,343, filed on Mar. 9, 2020.

(51) Int. Cl.
| | |
|---|---|
| *H04B 17/318* | (2015.01) |
| *G16H 50/80* | (2018.01) |
| *G16H 40/67* | (2018.01) |
| *G06F 16/23* | (2019.01) |
| *G16H 10/65* | (2018.01) |
| *H04W 4/80* | (2018.01) |

(52) U.S. Cl.
CPC ......... *G16H 50/80* (2018.01); *G06F 16/2379* (2019.01); *G16H 10/65* (2018.01); *G16H 40/67* (2018.01); *H04B 17/318* (2015.01); *H04W 4/80* (2018.02)

(58) Field of Classification Search
CPC .... H04B 17/318; G16H 10/65; G06F 16/2379
See application file for complete search history.

(56) References Cited

U.S. PATENT DOCUMENTS

| | | | |
|---|---|---|---|
| 10,070,179 B2 * | 9/2018 | Brown | ............... H04N 21/4667 |
| 2013/0275160 A1 * | 10/2013 | Lev | .......................... G16H 50/80 |
| | | | 705/3 |
| 2014/0115310 A1 * | 4/2014 | Smith | ...................... G06F 3/06 |
| | | | 713/2 |

(Continued)

*Primary Examiner* — Myron Wyche
(74) *Attorney, Agent, or Firm* — Knobbe, Martens, Olson & Bear LLP (57) ABSTRACT

Contract tracing systems and methods for infectious disease tracking are disclosed. An infectious disease tracking system includes a plurality of user devices, each user device configured to detect, using a wireless communication module, a signal emitted by another one of the plurality of user devices. The user device can determine that a strength of the signal exceeds a predetermined event initiation signal strength threshold corresponding to a physical proximity between users of the devices and can store a contact tracing event record in response to determining that the strength of the signal exceeds the predetermined event initiation signal strength threshold. The user device can transmit the contact tracing event records to a data center where they can be stored and used to identify close contacts when an index case of an infectious disease is identified.

25 Claims, 5 Drawing Sheets

(56) References Cited

U.S. PATENT DOCUMENTS

| | | | |
|---|---|---|---|
| 2014/0171118 A1* | 6/2014 | Marti | H04W 4/021 |
| | | | 455/456.3 |
| 2016/0116343 A1* | 4/2016 | Dixon | G08B 29/26 |
| | | | 250/342 |
| 2017/0064618 A1* | 3/2017 | Katar | H04W 8/02 |
| 2017/0206334 A1* | 7/2017 | Huang | G16H 50/30 |
| 2018/0181091 A1* | 6/2018 | Funk | G08G 1/07 |

* cited by examiner

CONTACT TRACING SYSTEMS AND METHODS FOR TRACKING OF SHIPBOARD PATHOGEN TRANSMISSION

CROSS-REFERENCE TO RELATION APPLICATIONS

This application claims the benefit of U.S. Provisional Application Ser. No. 62/987,343, filed Mar. 9, 2020, titled "CONTACT TRACING SYSTEMS AND METHODS FOR TRACKING OF SHIPBOARD PATHOGEN TRANSMISSION," which is incorporated by reference herein in its entirety.

BACKGROUND

Technological Field

The present application relates to systems and methods for shipboard contact tracing upon identifying that a guest of a current or a prior voyage is an index case having a communicable disease.

Background

Contact tracing is the process of identifying persons who may have come into contact with an infected person ("contacts") and subsequent collection of further information about these contacts. By tracing the contacts of infected individuals, testing those contacts for infection, treating the infected and tracing their contacts in turn, public health system seek to reduce and halt the spread of infectious disease within a population. Contact tracing can be performed for many different types of infectious diseases, including vaccine-preventable and highly-transmissible infections like measles, various forms of gastroenteritis (for example, norovirus), and novel infections (for example, COVID-19, SARS-CoV, and SARS-CoV-2).

SUMMARY

In a first aspect of the present technology, an infectious disease tracking system for a cruise ship comprises a plurality of user devices, each user device comprising a wireless communication module, one or more processors, and memory storing computer-executable instructions. When executed by the one or more processors, the instructions cause the one or more processors to at least detect, using the wireless communication module, a signal emitted by another one of the plurality of user devices; determine that a strength of the signal exceeds a predetermined event initiation signal strength threshold; store, in the memory, a contact tracing event record in response to determining that the strength of the signal exceeds the predetermined event initiation signal strength threshold; and transmit the contact tracing event record.

In some embodiments, storing the contact tracing event record comprises storing an initial contact tracing event data point including at least a timestamp and an identifier of the other one of the plurality of user devices, updating the contact tracing event record by storing additional contact tracing event data points based on subsequent signals received from the other one of the plurality of user devices, and terminating storage of additional contact tracing event data points. In some embodiments, the instructions further cause the one or more processors to compare strengths of the subsequent signals to an event interruption signal strength threshold, and the storage of additional contact tracing event data points is terminated based at least in part on at least one of the subsequent signals having a strength below the event interruption signal strength threshold. In some embodiments, the storage of additional contact tracing event data points is terminated based on the strengths of the subsequent signals remaining below the event interruption signal strength threshold for at least a predetermined grace period. In some embodiments, the grace period is 90 seconds. In some embodiments, the instructions further cause the one or more processors to at least suspend the storage of additional contact tracing event data points based on a first one of the subsequent signals having a strength below the event interruption signal strength threshold, and resume the storage of additional contact tracing event data points in response to detecting a second one of the subsequent signals having a strength above the event interruption signal strength threshold prior to the expiration of a predetermined grace period. In some embodiments, the event interruption signal strength threshold is lower than the event initiation signal strength threshold. In some embodiments, the event initiation signal strength threshold is a Received Signal Strength Indicator value of −68 decibel-milliwatts (dBm), and wherein the event interruption signal strength threshold is lower than −68 dBm.

In some embodiments, the event initiation signal strength threshold comprises a predetermined Received Signal Strength Indicator (RSSI) value. In some embodiments, the contact tracing event record comprises a plurality of contact tracing event data points, each contact tracing event data point comprising at least a timestamp and an RSSI value. In some embodiments, the event initiation signal strength threshold is −68 decibel-milliwatts (dBm).

In some embodiments, the contact tracing event record indicates at least a duration of a contact tracing event and an identifier of the other one of the plurality of user devices or of a user thereof. In some embodiments, the instructions further cause the one or more processors to modify the contact tracing event record to indicate a close contact based on the duration exceeding a predetermined close contact time threshold. In some embodiments, the close contact time threshold is one of 5 minutes or 15 minutes.

In some embodiments, the wireless communication module of each user device is configured to communicate with the wireless communication modules of the other user devices using Bluetooth Low Energy (BLE) protocol.

In some embodiments, the system further comprises a plurality of wireless access points disposed within the cruise ship and configured to receive the transmitted contact tracing event record. In some embodiments, the plurality of wireless access points are configured to communicate with each of the user devices using Bluetooth Low Energy (BLE) protocol. In some embodiments, the instructions cause the one or more processors to store a plurality of contact tracing event records and to transmit a set of most recent contact tracing event records to an individual wireless access point of the plurality of wireless access points in response to detecting the individual wireless access point. In some embodiments, each of the plurality of wireless access points is in communication with a server and configured to transmit the received contact tracing event records to the server. In some embodiments, the server is configured to store each contact tracing event record in a data store in association with an identifier of the user device that generated the contact tracing event record or of a user thereof. In some embodiments, the server is further configured to store, in the data store, an association between each contact tracing event record and an identifier of a second user device identified in the contact tracing event record or of a user thereof. In some embodiments, the server is further configured to identify pairs of contact tracing event records generated by different user devices corresponding to a same contact tracing event, based at least in part on timestamps included within the pairs of contact tracing event records. In some embodiments, the server is further configured to perform deduplication based on the identified pairs of contact tracing event records. In some embodiments, the server is further configured at least receive an identification of a user identified as an index case user of an infectious disease; query the data store, in response to the identification of the user, to determine a set of close contact users having close contact records associated with the index case user; and output a contact tracing result identifying the set of close contact users.

In some embodiments, the system further comprises a server and a plurality of wireless access points disposed within the cruise ship, each wireless access point configured to wirelessly receive the contact tracing event records from the user devices and to transmit the received contact tracing event records to the server, wherein the server is further configured to at least store the contact tracing event records in a data store; receive an identification of a user identified as an index case user of an infectious disease; query the data store, in response to the identification of the user, to determine a set of close contact users having close contact records associated with the index case user; and output a contact tracing result identifying the set of close contact users.

In a second aspect of the present technology, an infectious disease tracking system for a cruise ship comprises a plurality of wireless access points disposed within the cruise ship and a server, each wireless access point of the plurality of wireless access points comprising a communication module configured to detect and identify mobile devices in proximity to the wireless access point, and a processor in communication with the communication module, the processor configured to cause storage, in a data store, of a location data point each time a mobile device is detected. Each location data point comprises a timestamp, an association with the wireless access point, and an association with a user corresponding to the mobile device. The server is in communication with the data store and is configured to receive an identification of a first user determined to be an index case of a disease; determine, based on the timestamps and the wireless access points corresponding to a plurality of location data points associated with the first user, a movement profile corresponding to the first user; identify, based on the movement profile, one or more additional location data points indicative of a possible contact with the first user, each of the one or more additional location data points associated with a user other than the first user; and determine, based on the one or more additional location data points, a set of second users who may have come into contact with the first user.

In some embodiments, the server is further configured to determine movement profiles corresponding to the second users. In some embodiments, the server is further configured to determine, based at least in part on the movement profiles corresponding to the second users, a set of third users who may have come into contact with one or more of the second users. In some embodiments, the server is further configured to generate, based at least in part on the set of second users, the set of third users, and a passenger manifest of the cruise ship, a list of passengers who have not come into contact with the first user or the one or more other users who have come into contact with the first user. In some embodiments, the server is further configured to generate, based at least in part on the set of second users and the set of third users, a list of passengers to be quarantined.

In some embodiments, each of the mobile devices comprises one or more of a personal computing device or a wearable electronic device.

In some embodiments, the communication module of each wireless access point is configured to detect and identify mobile devices using one or more of near Bluetooth, Bluetooth Low Energy (BLE), near-field communication (NFC), Wi-Fi, radio-frequency identification (RFID), or a wireless broadband communication protocol.

In some embodiments, each of the one or more additional location data points is identified if the additional location data point is associated with the same wireless access point and has a timestamp within a threshold time relative to at least one of the location data points associated with the first user.

In some embodiments, the server is further in communication with an imaging system that records images or video of areas of the cruise ship where the wireless access points are located. In some embodiments, the server is further configured to obtain, from the imaging system, an image or video file corresponding to each of the additional location data points; and store an association between each image or video file and the second user associated with the corresponding additional location data point. In some embodiments, the imaging system is further configured to determine facial recognition results based on images captured by the imaging system, wherein the infection control system is further configured to identify second users based on the facial recognition results.

In some embodiments, the system retains the location data points in the data store for a predetermined retention period. In some embodiments, the predetermined retention period is one month. In some embodiments, the system retains the location data points stored in the data store during a first voyage of the cruise ship until at least the end of a subsequent voyage of the cruise ship.

DETAILED DESCRIPTION

Contact tracing seeks to disrupt ongoing transmission and reduce the spread of an infectious disease. Contract tracing generally involves the following steps:

An individual ("index case") is identified as having a communicable disease. This case may be reported to public health authorities or managed by the primary health care provider.

The index case is interviewed to learn about the index case's movements and with whom the index case has been in close contact within a specific time period of interest.

Depending on the disease and the context of the infection, family members, health care providers, and anyone else who may have knowledge of the case's contacts may also be interviewed.

Once contacts are identified, public health workers contact the identified contacts to offer counseling, screening, preventative care, and/or treatment.

Contacts may be isolated (for example, quarantined in a hospital setting or required to remain at home) or excluded (for example, prohibited from attending a particular location, like a school) if deemed necessary to control the spread of the infectious disease.

If contacts are not individually identifiable (for example, members of the public who attended the same location), broader communications may be issued, such as media advisories.

In cases of novel infectious disease, contact tracing can also generate important data on characteristics of the disease, such as infectiousness and incubation period. Typical forms of contact tracing are time consuming, manpower-intensive, and cumbersome. Contact tracing requires great speed and accurate information to be effective, but often results in an incomplete or inaccurate list of contacts. One of the most significant drawbacks to typical forms of contact tracing is the time it takes to identify individuals who may have been in close contact with the index case.

The present disclosure is directed to systems and methods for rapid contact tracing on a vessel, such as but not limited to a cruise ship. Embodiments of the present disclosure can be implemented in many different settings, including but not limited to hospitals and other health-care settings, apartment buildings, office buildings, prisons, amusement parks, and entertainment venues, such as athletic arenas and concert venues. A combination of systems, such as facial recognition systems, Bluetooth Low Energy (BLE) systems, and RFID systems, are used to collect person-specific data for each person that is physically present within a defined space (such as all crewmembers and guests that are physically present on a particular cruise ship) or is associated with a defined population (such as all guests that have embarked on a particular voyage of a particular cruise ship).

In some examples, this person-specific data is collected for each guest and crewmember from start to finish of a voyage of a cruise ship. Upon identification of a guest or crewmember as an "index case" having a communicable disease, a map of the physical location within the defined space (hereinafter referred to as a "movement profile") is calculated for the index case, using the person-specific data collected for the index case. A movement profile can include information on the physical location of a person within the defined space at all points in time, or for all points in time for which person-specific data is available.

In some implementations of the present technology, a movement profile is next calculated for all persons that are physically present within a defined space (such as all crewmembers and guests that are physically present on a particular cruise ship) or are associated with a defined population (such as all guests that have embarked on a particular voyage of a particular cruise ship). These movement profiles can be calculated using each individual's person-specific data that has been collected during a particular voyage of the cruise ship.

Embodiments of the present disclosure perform rapid contact tracing by comparing the movement profile of the index case to the movement profiles of all other individuals of interest. Individuals of interest can include, for example, all guests and crew members physically present on a particular cruise ship at a given point in time, all guests and crew members that embarked on a particular voyage of a particular cruise ship (whether or not those individuals have since disembarked the cruise ship), and all guests and crew members that were embarked on an immediately-preceding voyage of the particular cruise ship. As a result of comparing the movement profile of the index case with the movement profile of other individuals of interest, individuals of interest who were proximate to or came in close contact with (in one example, within a defined number of feet of) the index case are identified as a "close contact." Embodiments of the present disclosure include identifying further "close contacts" by comparing the movement profile of an identified "close contact" to the movement profiles of all other individuals of interest. In this way, "close contacts" of an index case are rapidly and accurately identified in a shipboard context.

The term "close contact" could be defined by medical personnel onboard as well as public health officials to mean 0 to X number of feet, depending on the type of communicable disease. In one non-limiting example, an individual is deemed to have close contact with an index case if the individual came within zero to three feet of the index case. In another non-limiting example, an individual is deemed to have close contact with an index case if the individual came within zero to six feet of the index case. The distance threshold may be selected (e.g., by a medical officer or other crew member) based on specific transmission characteristics of the particular pathogen or disease. The distance threshold can be selected based on guidance provided by public health officials.

In other implementations of the present technology, a movement profile is next calculated for a subset of persons rather than all persons present within a defined space or associate with a defined population. For example, if the movement profile of the index case indicates that the index case was not physically present on Decks 1, 2, and 3 during the duration of a particular cruise, a movement profile may not be calculated for individuals who are known to have only been present on Decks 1, 2, and/or 3 during the duration of the voyage.

In some embodiments of the present technology, contact tracing events are recorded based on interactions between mobile devices carried by users (e.g., guests, crewmembers, or any other persons present within the defined space or population). For example, each user present within the defined space may carry a mobile device such as a dedicated wearable device, a smartphone, tablet, or other computing device, or the like. The mobile devices may be configured to detect other mobile devices within a determined proximity (e.g., using any suitable wireless communication protocol such as Bluetooth, Bluetooth Low energy, RFID, Wi-Fi, or the like) and to record contact tracing events based on the detected mobile devices according to various algorithms as described herein. In one example, contact tracing events may be recorded and/or determined to be "close contacts" at each mobile device when another device is detected within a predetermined proximity threshold and/or for at least a threshold time (e.g., a close contact time threshold). In some embodiments, the proximity of another mobile device may be determined based on a measurable quantity such wireless signal strength. As will be described in greater detail, suitable algorithms for recording contact tracing events and determining close contacts may be implemented so as to avoid or reduce the recording of false positive close contacts and/or the failure to record close contacts based on false negative contact tracing events.

Advantages of the systems and methods described herein include enhanced speed and accuracy of contact tracing in the shipboard context, and the ability to implement narrowly-tailored quarantines in lieu of ship-wide quarantines. Public health policies that are currently implemented in the event of a communicable disease in the shipboard context typically impose a ship-wide quarantine of all guests and crew members that are physically present on a particular cruise ship associated with a currently-embarked or previously-embarked index case. Such ship-wide quarantines have been demonstrated to increase, rather than reduce, the communication of infectious disease within the ship. In implementations of the present disclosure, individuals who are identified as "close contacts" (either by direct association with the index case as demonstrated by recorded contact tracing events, proximate movement profiles or by indirect association with the index case via an intermediary close contact) can be quickly isolated using narrowly-tailored person- or group-specific quarantines. Individuals who are not identified as "close contacts" can be isolated from "close contacts" by, for example, rapid disembarkation from the ship or isolation in a particular area of the ship. If appropriate or required by public health officials, such individuals who are not subject to person- or group-specific quarantines onboard the ship can self-quarantine for a period of time following disembarkation from the ship, without experiencing days, and in some cases weeks, of increased risk of exposure to the infectious disease onboard the ship.

Implementations of the present disclosure can give the ship's leadership, such as the captain and the medical officer, the ability to perform contact tracing without the use of outside resources, such as shoreside resources. Because embodiments of the present disclosure provide ship operators with ship-initiated and ship-implemented contact tracing, valuable time is not lost while the ship waits for shoreside contract tracing resources. The data-driven nature of contact tracing according to the present disclosure also results in a highly accurate list of close contacts. This enables the ship's leadership to implement narrowly-tailored quarantine measures onboard as soon as a single index case is identified, and to report to each port of call or health authorities as may be necessary. Shoreside employees of the cruise operators may, in some cases, access information generated by the systems and methods described herein, for example to view reports, or—should the need arise—to run the reports shoreside.

Systems for Collecting Location Data

Systems and methods of the present disclosure include systems configured to collect data on the location of a person within a bounded space such as a cruise ship, hotel, stadium, office building or airport, to name a few examples. The data pertaining to the location of a person can be obtained using object location and tracking systems, imaging systems configured to obtain image or video files, other location tracking technologies, or a combination of these technologies.

Figure 1:
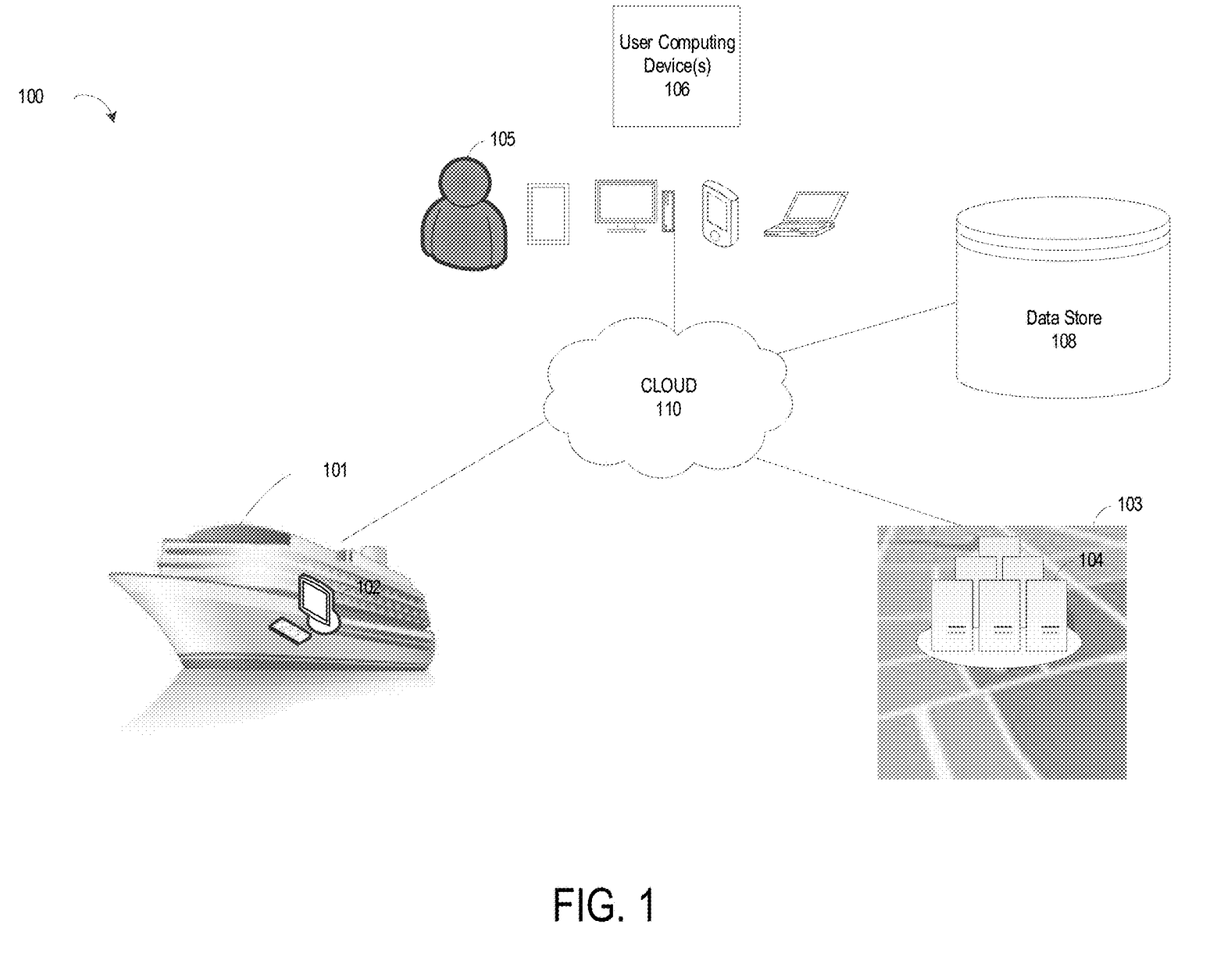
FIG. 1 schematically illustrates an example of a networked computing system comprising a ship-based computing system and a shore-based computing system in accordance with the present technology.

FIG. 1 illustrates a diagram of an example networked computing system 100 within which the contact tracing systems and methods described herein may be implemented. The system 100 includes a ship-based computing system 102 which may be in communication with a shore-based computing system 104 via a cloud-based or wireless network 110, according to this exemplary embodiment. In some embodiments, the ship-based computing system 102 is located on a ship 101 (or other mass transport, such as a train, a shuttle, a bus, a plane, and so forth) configured to transport a plurality of individuals (e.g., users of mobile devices such as guests, crewmembers, or others) during a trip or voyage. The ship-based computing system 102 may include any number of individual independent and/or networked computing devices located within the ship 101, such as user computing devices 106. The shore-based computing system 104 is located in a shore-based facility 103 and is associated with a service provider, such as a company or entity that operates the ship 101. Alternatively, or additionally, the shore-based computing system 104 may include a cloud-based database or data store 108 with which the ship-based computer system 102 communicates at least periodically while in port or at sea. Alternatively or in addition, the shore-based computing system 104 may include a cloud-based computing system with which the ship-based computer system 102 communicates at least periodically.

The system 100 may also include a plurality of user computing devices 106 that are operated by customers and/or agents of the service provider (e.g., any person present within the defined environment such as the ship 101 such as a guest or crewmember). The user computing devices 106 may include any one of a wearable device (e.g., a dedicated wearable device for contact tracing and/or a wearable device configured for functions such as access credentialing and/or purchasing or accessing services or products), a smartphone, a tablet, a laptop, a desktop, a personal digital assistant (PDA), a vehicle communication system, a smartwatch, or any other electronic device. The user computing device 106 allows for the determination of contact tracing events and/or location data points for a user 105 (for example, the guest or crewmember, as described above) based on the user's movements and/or proximity to other users 105 while the user 105 is embarked on the ship 101 during a sailing. Any suitable communications arrangement can be implemented in embodiments of the present technology.

The shore-based computing system 104 and/or the ship-based computing system 102 can also store data relating to each user that is embarked on or has sailed on a particular sailing. User-specific data can include, but is not limited to, contact tracing events and/or "close contacts" determined based on contact tracing events.

Figure 2:
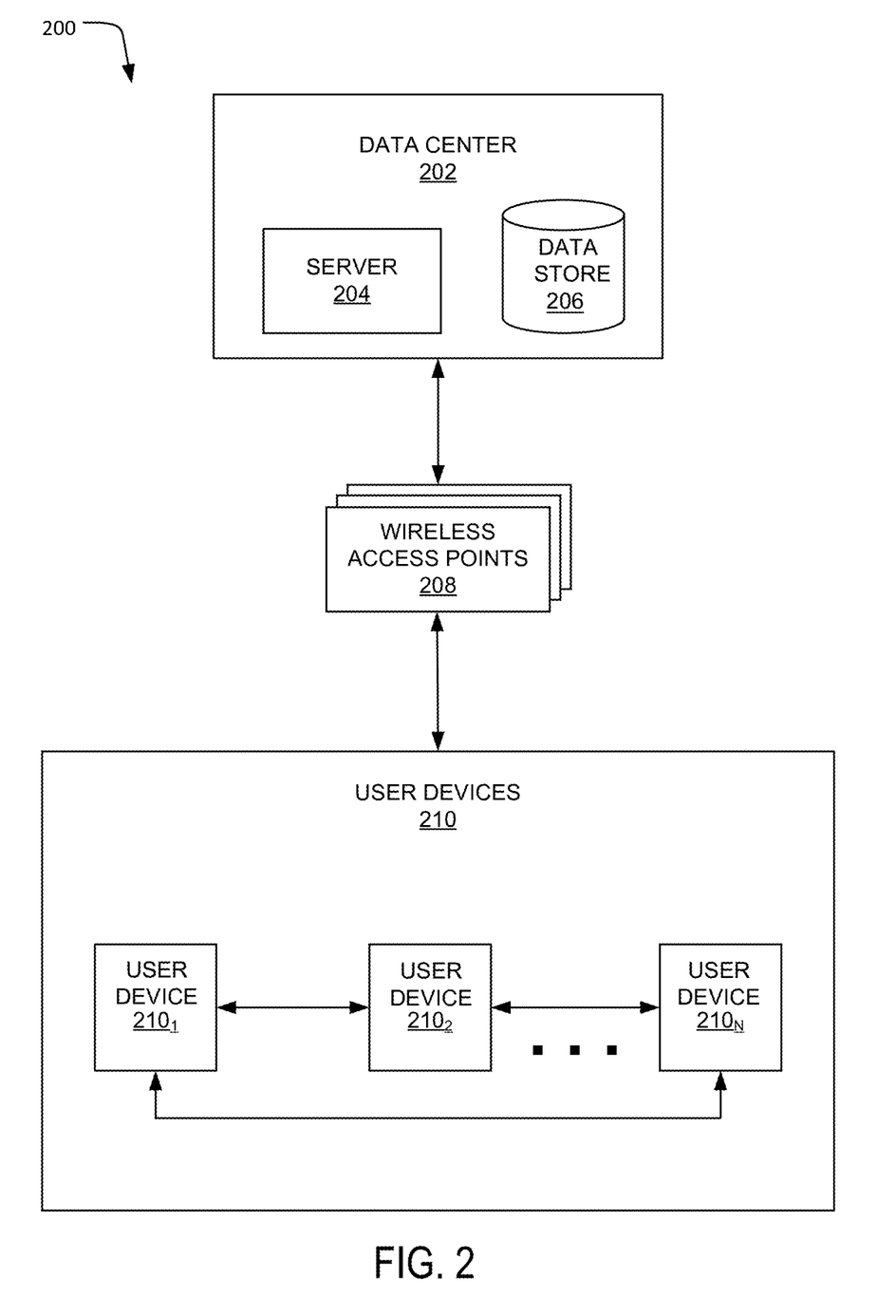
FIG. 2 schematically illustrates an example system for tracking of shipboard pathogen transmission in accordance with the present technology.

FIG. 2 schematically illustrates an example system 200 for tracking of shipboard pathogen transmission in accordance with the present technology. The system 200 may be, for example, the ship-based computer system 102 of FIG. 1 or a portion thereof. The system 200 includes a data center 202, including a server 204 and a data store 206, as well as one or more wireless access points 208 and a plurality of user devices 210 (e.g., user devices $210_1$, $210_2$, ... $210_N$).

The data center 202 can include one or more computing devices, including at least a server 204 and a data store 206. The server 204 is configured to communicate via wired and/or wireless communications, directly or indirectly, with any or all of the wireless access points 208. The server 204 and/or one or more other computing devices of the data center 202 are configured to perform various processing, analysis, and/or storage operations as described herein. The data store 206 stores contact tracing event records and/or close contact records based at least in part on data uploaded from the user devices 210 via the wireless access points 208. In some embodiments, the data store 206 stores user information for individual users (e.g., guests, crewmembers, or others) such as user identifiers, travel party information, itinerary information, user movement profile information, interaction information, contact tracing event records associated with individual users, and/or close contact records associated with individual users.

The server 204 may be configured to receive contact tracing event records and/or close contact records from the wireless access points 208 on a continuous or periodic basis and to cause the received contact tracing event records and/or close contact records to be stored in the data store 206 in association with user information stored therein. For example, a received contact tracing event record or close contact record may have been generated at a first user device associated with a first user, and may include an identifier of a second user device associated with a second user that was detected within a threshold distance. In response to receiving the record, the server 204 can cause the record to be stored in the data store 206 in association with both the first user and the second user.

In order to avoid duplicate records in the event that the second user's user device also recorded a contact tracing event record or close contact record based on the same interaction, the server 204 can further perform deduplication of records. For example, the server 204 may determine not to cause an additional record to be stored, based on the record from the first user device, if a record of interaction with the second user device already exists for the first user device with an overlapping timestamp (e.g., based on a previously received record from the second user device). In some embodiments, upon detection of a duplicate record, the server 204 may alter the preexisting record such as by changing the total duration of the recorded contact tracing event. For example, if the timestamp ranges of the two duplicate events overlap but are not identical, the server 204 may record the full union of the two timestamp ranges as the duration of the contact tracing event. In some cases, this implementation of the union function may cause an existing contact tracing event record, which was of insufficient duration to be considered a close contact, to be converted to a close contact record if the union of the two timestamp ranges is greater than the close contact time threshold.

The wireless access points 208 may be disposed at various locations through the ship or other defined environment where they may detect and communicate wirelessly with user devices 210. In some embodiments, the wireless access points 208 may be strategically placed so as to increase the probability of contacting most or all of the user devices 210. For example, in a cruise ship implementation, wireless access points 208 may be placed in common areas where many guests and crewmembers pass or congregate. In one example, at least some wireless access points 208 may be placed in corridors leading to staterooms, in corridors leading to crew accommodations, in dining facilities, and the like. In another example, a wireless access point 208 may be placed at or near each location on the ship where guests and crewmembers can disembark.

The wireless access points 208 may be configured with any one or more wireless communication protocols suitable for communicating with the user devices 210 and/or other devices. For example, the wireless access points 208 may be configured to communicate with the user devices 210 using any one or more of Bluetooth, Bluetooth Low Energy (BLE), Wi-Fi, RFID, or other suitable wireless communication protocol. In some embodiments, the wireless access points 208 are dedicated wireless access points 208 for a contact tracing system (e.g., BLE devices configured to communicate with the user devices 210 via BLE). In other implementations, the wireless access points 208 may be multi-function devices. For example, the wireless access points 208 may be configured to communicate with the user devices 210 via BLE while also being configured to provide other wireless access services such as a local area wireless network for internet access.

Each wireless access point 208 can include a wireless communication interface, one or more processors and one or more memory devices including computer-executable instructions that cause the one or more processors to detect individual user devices 210 within a suitable range for reliable data transmission and, upon detection, to cause the individual user devices 210 to upload contact tracing event records and/or close contact records stored thereon. The one or more memory devices can further be configured to store the records uploaded from the user devices 210 at least until the records are transmitted to the data center 202. In various embodiments, the wireless access points 208 can transmit the received records to the data center 202 immediately upon receipt from the user devices 210, or may be configured to store the received records locally and transmit a larger set of received records to the data center 202 when a threshold number of records is reached and/or at a specified time according to a predetermined upload schedule.

The user devices 210 are mobile devices configured to be carried by individual users throughout the predetermined environment. In some embodiments, the user devices may be dedicated contact tracing user devices, for example, wearable devices such as wristbands, neck worn devices, or the like. Wristbands may be especially suitable for contact tracing implementations, as a single-use wristband may be worn at all times during a sailing (e.g., over a duration of several days, up to two weeks or longer) without inconveniencing the wearer. Alternatively, in some embodiments the user devices 210 may be personal computing devices such as smartphones or tablets having an application executing thereon that causes the personal computing device to perform the functions of the user device 210 described herein. In some embodiments, the user devices 210 may be ruggedized (e.g., waterproof, water resistant, etc.). The user devices 210 may be rechargeable, and/or may be designed as relatively low-energy devices having sufficient battery life to operate for the duration of a sailing without needing to be recharged, so as to facilitate reliable operation of the devices throughout the sailing and to avoid barriers to user compliance and participation.

In cruise ship implementations, the system 200 may include a large number of user devices 210 (e.g., up to hundreds or thousands of user devices 210). The system 200 may include a suitable number of user devices 210 such that a user device 210 is issued to every user aboard the ship (e.g., every person, every adult, or every person above a threshold age, including both guests and crewmembers).

Figure 3:
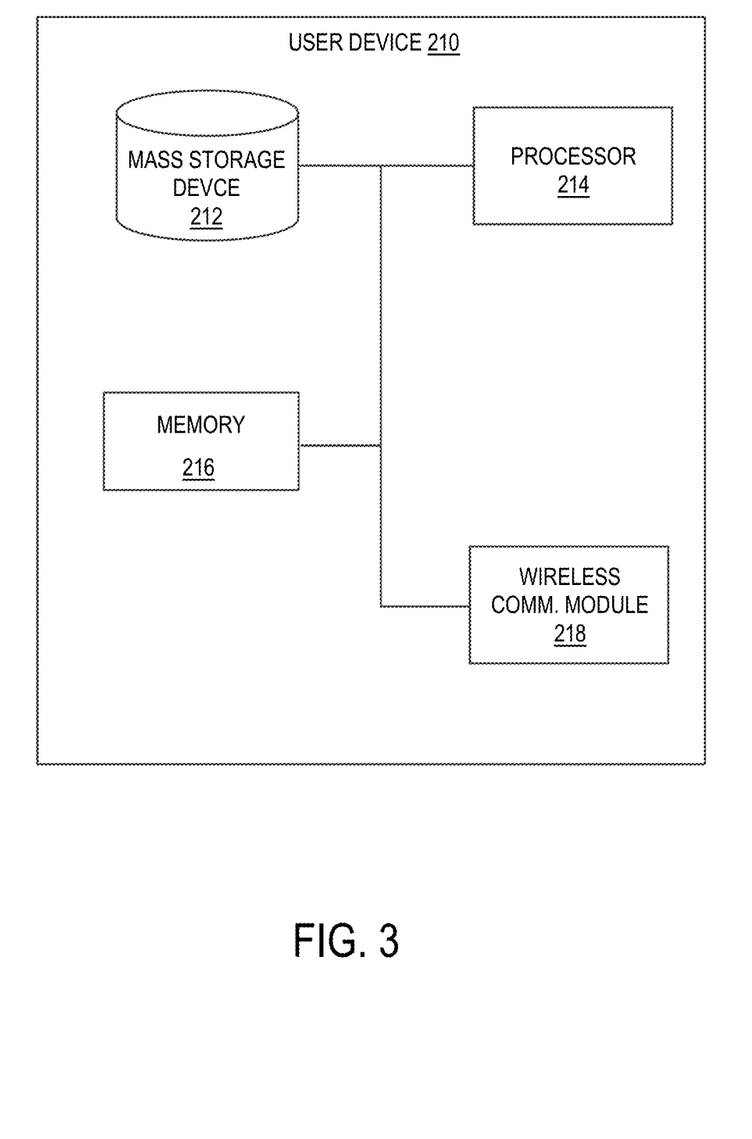
FIG. 3 schematically illustrates an example user device configured for tracking of shipboard pathogen transmission in accordance with the present technology.

FIG. 3 schematically illustrates an example user device 210 configured for tracking of shipboard pathogen transmission in accordance with the present technology. The user device 210 includes at least a mass storage device 212, a processor 214, a memory 216, and a wireless communication module 218. The memory 216 can store computer-executable instructions that, when executed by the processor 214, cause the processor to detect other user devices 210 nearby using the wireless communication module 218. The wireless communication module 218 may be configured for any suitable wireless communication protocol, such as Bluetooth, BLE, RFID, Wi-Fi, or the like.

When another user device 210 is detected (e.g., based on wireless communications between the wireless communication module 218 and the wireless communication module 218 of a nearby second user device 210), the processor 214 may implement one or more algorithms stored in the memory 216 to generate contact tracing event records and/or close contact records based on the wireless communications between the two user devices 210. The processor 214 can further cause the generated contact tracing event records and/or close contact records to be stored in the mass storage device 212.

The wireless communication module 218 is further configured to detect and communicate with wireless access points 208 (FIG. 2). Based on detecting a wireless access point 208, the processor 214 is configured to cause the wireless communication module 218 to transmit contact tracing event records and/or close contact records from the mass storage device 212 to the wireless access point 208. In various embodiments, the user device 210 may be configured to transmit the records stored in the mass storage device 212 each time a wireless access point 208 is detected, or may selectively transmit the records on a time-based schedule. For example, when a wireless access point 208 is detected, the user device 210 may be configured to transmit stored records only if a periodic interval (e.g., 1 minutes, 5 minutes, 10 minutes, 30 minutes, 1 hour, 2 hours, 6 hours, 12 hours, 24 hours, or any other suitable threshold time) has elapsed since the most recent upload of records to a wireless access point 208. In another implementation, a time-based schedule may be implemented by programming the user device 210 to stop searching for wireless access points 208 after each upload, and to resume searching and/or detecting wireless access points 208 after the periodic interval elapses.

After each upload to a wireless access point 208, the uploaded records may be retained within the mass storage device 212 or may be erased. In some embodiments, the user device 210 may be configured to upload only the records that were stored subsequent to a timestamp associated with the most recent upload. In the event that a user device 210 stores enough contact tracing event records to exceed the storage capacity of the mass storage device 212, the processor 214 may be configured to erase or overwrite the oldest stored records in order to store new contact tracing event records as they are recorded.

Data Collection using Object Location and Tracking

In one example implementation, an infectious disease tracking system of the present disclosure includes a plurality of wireless access points disposed within a cruise ship. Each wireless access point of the plurality of wireless access points includes a communication module configured to detect and identify mobile devices in proximity to the wireless access point. Each wireless access point of the plurality of wireless access points also includes a processor in communication with the communication module. The processor is configured to cause storage, in a data store, of a location data point each time a mobile device is detected. Example mobile devices include, but are not limited to, a personal computing device and a wearable electronic device. In one non-limiting example, all individuals embarked on a cruise ship are required to wear a personal electronic device during the time individual is embarked on the cruise ship. Such personal electronic devices can be distributed at the time of embarkation and collected at the time of debarkation. In another example, such personal electronic devices can be distributed when an individual onboard a voyage, or an immediately-preceding voyage, is identified as an index case Each location data point includes a timestamp, an association with the wireless access point, and an association with a user corresponding to the mobile device. The user can include, for example, a guest or crewmember onboard the cruise ship. The communication module of each wireless access point can be configured to detect and identify mobile devices using one or more of near Bluetooth, Bluetooth Low Energy (BLE), near-field communication (NFC), Wi-Fi, radio-frequency identification (RFID), or a wireless broadband communication protocol.

One of the main concerns with implementing such technology on a ship is that BLE/RFID technology bleeds from deck to deck on ships as opposed to apartment buildings, given the proximity of the access points and the thin layer materials used in shipbuilding. So it may be necessary to isolate and discard signals that are coming from other decks. In other words, a guest walking through a hallway on Deck 5 may be picked up by a BLE Access Point in Deck 4, but technology solutions are described in U.S. Pat. No. 10,645,536 that help solve this problem. Example systems and methods for object location and tracking that can be implemented in the present disclosure are described in U.S. Pat. No. 10,645,536, which is incorporated herein by reference in its entirety.

Data Collection using Facial Recognition Systems

Data pertaining to the location of a person can be obtained using facial recognition systems. For example, an imaging system including cameras located throughout the ship can be configured to determine facial recognition results based on images captured by the imaging system. In some cases, images and video files obtained by the imaging system are used to identify that a particular individual, such as a guest or crew member, is present at a particular location within the cruise ship. Implementations of the present disclosure can use this location information to develop a movement profile corresponding to a particular individual of interest, such as an index case or individuals who may have come in close contact with the index case.

Advantageously, embodiments of the present disclosure can be implemented using just facial recognition technology because such technology currently covers most public spaces onboard a cruise ship. For example, cruise operators using computer vision technology can recognize guests in dining rooms and other generally crowded areas, such as a casino. Also, stateroom doors equipped with facial recognition technology, such as that described in U.S. Pat. No. 10,776,613, can provide facial recognition results in hallways. Although facial recognition would be limited to public area locations like the pools, casinos, restaurants, promenade, and hallways, a single movement profile can be accurately and effectively stitched together using facial recognition results from such public areas.

Example systems and methods for object location and tracking that can be implemented in the present disclosure are described in U.S. Pat. No. 10,776,613, which is incorporated herein by reference in its entirety.

Data Collection using Object Location and Tracking and Facial Recognition Systems Implementations of the present disclosure can process data collected from both objection location and tracking systems and facial recognition systems to develop a movement profile of an individual of interest, such as an index case or individuals who may have come in close contact with the index case.

In an example implementation, an infectious disease tracking system of the present disclosure includes an imaging system disposed within a cruise ship. The imaging system can record images or video of areas of the cruise ship, including areas where the plurality of wireless access points are located. The imaging system can be configured to determine facial recognition results based on images captured by the imaging system. The infection disease tracking system can include a server configured to obtain, from the imaging system, an image or video file corresponding to a location data point that is indicative of a possible contact with an index case. The index case's movement profile can include, for example, the location data point. The server is also configured to store an association between each image or video file and a user associated with the location data point that is indicative of the possible contact with the index case. The infectious disease tracking system can be configured to determine, based on the stored association, a set of individuals who may have come into contact with the index case. Such facial recognition results can also be used to enhance or increase confidence of location data obtained using object location and tracking systems.

Example Contact Tracing Implementations

Various example implementations of contact tracing methods based on the data collection systems of the present technology will now be described.

Contact Tracing Based on Detected Contact Tracing Events

Figure 4:
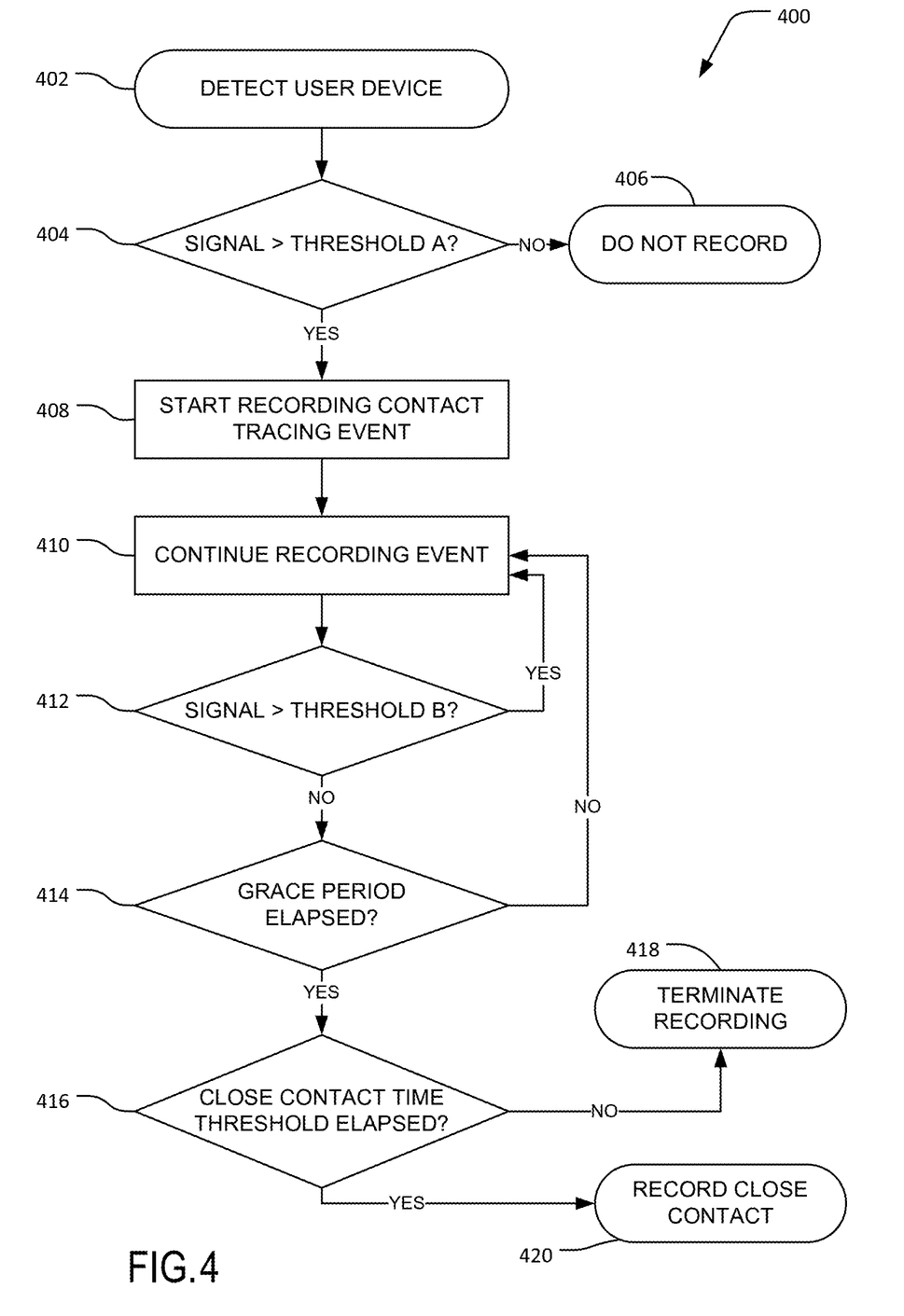
FIG. 4 is a flow chart illustrating an example algorithm for recording contract tracing events in accordance with the present technology.

FIG. 4 is a flow chart illustrating an example algorithm 400 for recording contract tracing event records and/or close contact records in accordance with the present technology. The algorithm 400 may be performed by any suitable computing device in the possession of a user. For example, the algorithm 400 may be implemented by any of the user devices 210 described with reference to FIGS. 2 and 3. In the context of the system 200 of FIG. 2, many or all of the user devices $210_1$, $210_2$, ... $210_N$ may each be configured to perform the algorithm 400 when they detect other user devices 210 nearby. In one particular example implementation, each of the user devices 210 is a Bluetooth Low Energy (BLE) enabled wearable device such as a wristband, worn by every guest (or every guest above a threshold age) and crewmember aboard a cruise ship. However, it will be understood that the algorithm 400 is not limited to this particular implementation.

The algorithm 400 begins at block 402 when another user device 210 is detected. For example, the wireless communication module 218 (e.g., a BLE communication device) of a first user device 210 may establish communication with the wireless communication module 218 of a second user device 210 within a suitable signal range (e.g., by continuously listening for other nearby devices). Based on detecting one or more signals from the wireless communication module 218 of the second user device 210, the processor 214 of the first user device 210 can begin executing the algorithm 400. In some cases, if both the first and second user devices 210 detect each other, both devices may begin executing the algorithm 400 simultaneously. When a second user device 210 is detected, the algorithm 400 continues to decision state 404.

At decision state 404, the processor 214 determines whether a strength of the signal received from the second user device 210 is greater than or equal to a first predetermined threshold (e.g., an event initiation signal strength threshold, referred to hereinafter as "threshold A"). Threshold A may be selected to correspond to a desired physical distance between the two user devices 210. For example, in some embodiments, threshold A may be selected to correspond to a distance such as 3 feet, 6 feet, 10 feet, 20 feet, or any other suitable distance associated with a heightened risk of pathogen transmission. It will be understood that suitable physical distance thresholds may evolve based on updated understandings of specific pathogen transmission times and methods, without departing from the spirit or scope of the present technology.

The event initiation signal strength threshold may be expressed in terms of a signal strength such as a Received Signal Strength Indicator (RSSI) value or other suitable unit of signal strength. The specific RSSI value of threshold A may be determined empirically for a set of user devices 210, for example, by measuring signal strength between two sample user devices 210 worn by users placed at the desired physical distance threshold. In one particular example, a set of user devices 210 may use a threshold such as −68 decibel-milliwatts (dBm) or other suitable value, as threshold A. Empirical adjustment of threshold A may be desirable to avoid false negatives, in which two users come close enough to transmit a pathogen, without their user devices 210 recording a contact tracing event record. In some embodiments, threshold A can be set low enough such that signal attenuation by the human body does not unduly prevent the generation of contact tracing event records.

If the signal strength is not greater than or equal to threshold A, the algorithm 400 terminates at block 406, and a contact tracing event is not recorded. If the signal strength is greater than or equal to threshold A, the algorithm 400 continues to block 408, where the user device 210 starts recording a contact tracing event. The processor 214 may store, in the mass storage device 212, a new contact tracing event record including an initial timestamp corresponding to a device time at which the detected signal exceeded threshold A. The record may further include other information such as an RSSI value of the signal, a device location, and/or an identifier of the second user device 210.

After the user device 210 has started recording the contact tracing event by establishing a contact tracing event record in the mass storage device 212, the algorithm 400 continues to block 410, where the user device 210 continues recording the contact tracing event. In some embodiments, the processor 214 continues adding data to the established contact tracing event record in the mass storage device 212. For example, the processor may add further paired RSSI-timestamp data points to the record at a periodic interval while the user device 210 continues to receive the signal from the second user device 210.

As the user device 210 continues recording the contact tracing event, the processor 214 continues to decision state 412, where it may continuously or periodically determine whether the signal strength is greater than or equal to a second predetermined threshold (e.g., an event interruption signal strength threshold, referred to hereinafter as "threshold B"), which may be the same as or different than threshold A. Threshold B may similarly be expressed in terms of a RSSI value in dBm, or any other suitable unit of received signal strength. As long as the signal remains above threshold B, the algorithm 400 continues to record the contact tracing event at block 410. If the signal strength dips below threshold B, the user device 210 may interrupt recording of the event.

Threshold B may be greater than, equal to, or lower than threshold A. However, it may be advantageous to set threshold B lower than threshold A in order to address certain shortcomings of the use of RSSI or other signal strength indicators as a method of measuring physical distance between people wearing user devices 210. Specifically, water, which makes up a large proportion of the human body, reliably absorbs frequencies in the 2.4 GHz range, resulting in significant signal attenuation when a user's body is disposed between their user device 210 and the second user device 210. Thus, it is likely that the signal strength will drop below threshold A, at least temporarily, one or more times while the two users remain within the selected physical proximity. Accordingly, the reliability of contact tracing event recording is improved by allowing the signal strength to drop temporarily below the threshold A that is used to initiate recording of a contact tracing event, without terminating the record.

If it is determined at decision state 412 that the signal strength is lower than threshold B, the algorithm continues to decision state 414, where a grace period begins elapsing. The grace period is a predetermined time interval that is allowed to pass before the user device 210 terminates recording of the contact tracing event. While the signal strength remains below threshold B, the processor 214 may suspend recording of data points (e.g., paired RSSI-timestamp data points) or may continue recording data points that include the sub-threshold B signal strength values. If the signal strength returns to a value greater than threshold B before the grace period elapses, the algorithm returns to block 410 and continues recording the event. If the grace period elapses without the signal strength returning to a value above threshold B, the contact tracing event is terminated, and the algorithm continues to decision state 416.

The grace period is a predetermined time period selected to allow for temporary periods of signal attenuation or increased distance between users during a contact tracing event. For example, if two users stand with six feet of each other for a relatively long time period (e.g., five minutes or more), but move to a greater distance (e.g., 20 feet apart) for a brief period (e.g., 30 seconds) in the middle of the five-minute time period, it is generally understood that such momentary distancing does not substantially reduce the probability of pathogen transmission during the five-minute time period. Thus, it is desirable to incorporate a grace period as described herein so as to reduce the occurrence of false negative results.

When the grace period has elapsed, the contact tracing event terminates and no additional data (e.g., paired RSSI-timestamp data points) are added to the contact tracing event record in the mass storage device 212. At decision state 416, the processor 214 determines, on the basis of the completed record, whether or not the recorded contact tracing event should be deemed a "close contact." To do so, the processor 214 can determine a timestamp range of the terminated record, and compare the range to a predetermined close contact time threshold. In some embodiments, the processor 214 may subtract the initial timestamp value recorded at block 408 from a final timestamp value (e.g., the final timestamp value recorded prior to the signal strength dropping below threshold B, the first timestamp value associated with a signal strength below threshold B, or a timestamp value recorded at the end of the grace period when the recording is terminated). The subtracted timestamp range, corresponding to the total elapsed time of the contact tracing event, is then compared to the close contact time threshold to determine if the event was a "close contact."

If the timestamp range is less than the close contact time threshold, the algorithm 400 terminates at block 418, where the recording is terminated without recording a close contact. In some embodiments, the non-"close contact" contact tracing event record may still be retained in the mass storage device 212 and sent to the data center 202 via a wireless access point 208 (e.g., for further analysis in conjunction with a corresponding contact tracing event record sent from the second user device 210). Alternatively, if the timestamp range is greater than or equal to the close contact time threshold, the algorithm 400 terminates at block 420, where the contact tracing event record is stored as a "close contact" in the mass storage device 212.

The close contact time threshold may be determined based on any desired standard for pathogen transmission. For example, the close contact time threshold may be selected based on a science-based recommendation, regulation, policy, or guideline from an applicable health authority, such as the World Health Organization (WHO), the Centers for Disease Control and Prevention (CDC), or any other appropriate state, national, or international governmental or non-governmental organization. Example close contact time thresholds may be, for example, 2 minutes, 5 minutes, 10 minutes, 15 minutes, 20 minutes, or more, and it will be understood that suitable close contact time thresholds may evolve based on updated understandings of specific pathogen transmission times and methods, without departing from the spirit or scope of the present technology.

Figure 5:
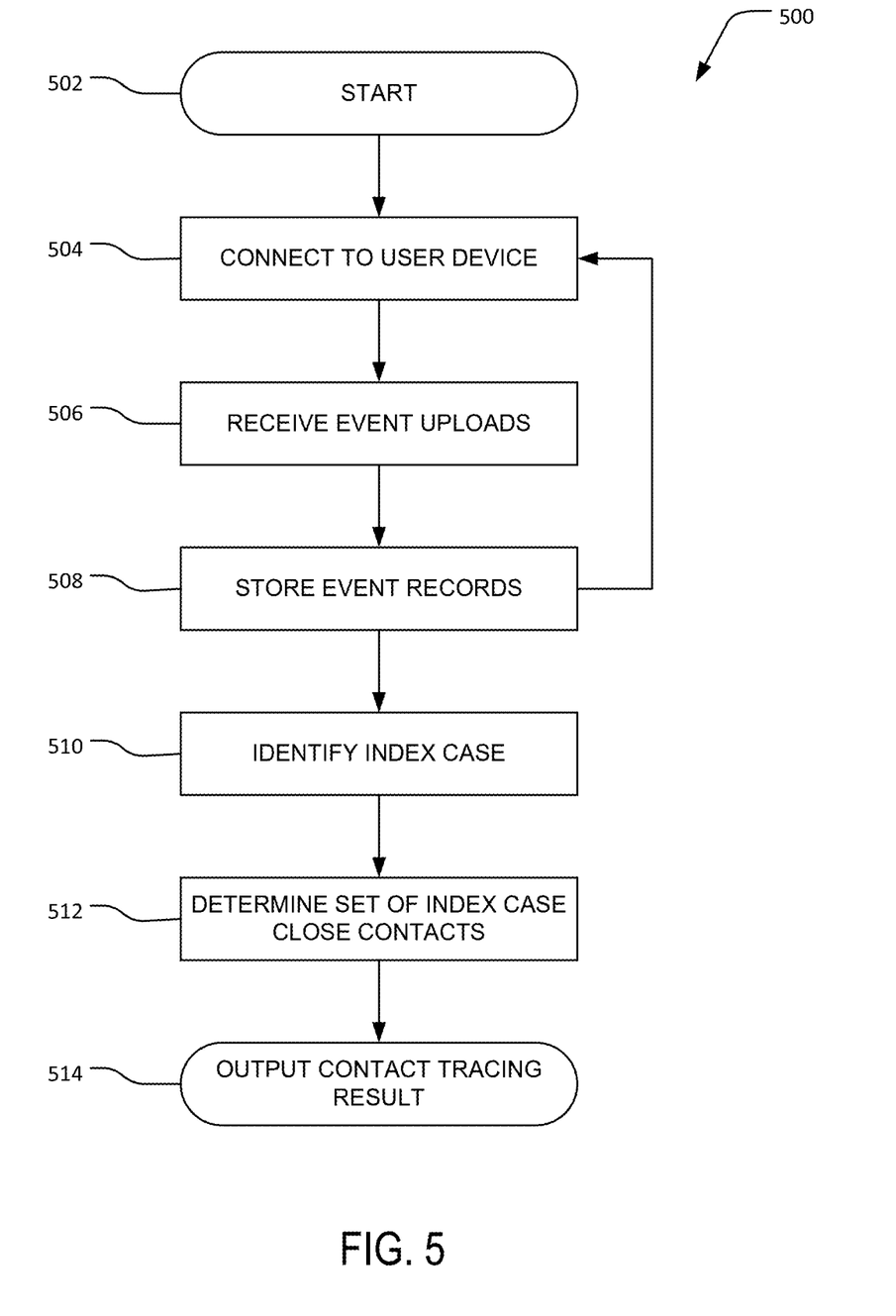
FIG. 5 is a flow chart illustrating an example method for contact tracing in accordance with the present technology.

FIG. 5 is a flow chart illustrating an example method 500 for contact tracing in accordance with the present technology. The method 500 may be performed by any suitable pathogen transmission tracking system. For example, the method 500 may be performed at least partially by the system 200 of FIG. 2 including a data center 202, a plurality of user devices 210, and wireless access points 208 configured to communicate with the data center 202 and the user devices 210. In one particular implementation, the system 200 is at least partially disposed within a cruise ship and each of the user devices 210 is a BLE enabled wearable devices such as a wristband, worn by every guest (or every guest above a threshold age) and crewmember aboard a cruise ship. However, it will be understood that the method 500 is not limited to this particular implementation.

The method 500 begins at block 502, which may coincide with the introduction of a plurality of users to a specified environment. For example, the method 500 may begin at block 502 when guests and crewmembers board a cruise ship. In some embodiments, the method 500 may be initiated as the first crewmembers board the ship, and additional user devices 210 may subsequently be added to the system 200 as additional crewmembers and the guests embark.

At block 504, one of the wireless access points 208 connects to one of the user devices 210. As described elsewhere herein, the user device 210 and the wireless access point 208 may connect using any suitable wireless communication protocol, such as Bluetooth, BLE, Wi-Fi, RFID, or the like. The user devices 210 may be configured to initiate the connection at block 504 on a periodic basis and/or based at least in part on detecting a wireless access point 208 within range.

After the wireless access point 208 and the user device 210 establish a wireless data connection, the method 500 continues to block 506, where the wireless access point 208 receives an upload of one or more contact tracing event records from the user device 210. Some or all of the contact tracing event records may be indicated as "close contacts." At block 508, the wireless access point 208 causes storage of the contact tracing event records. The wireless access point 208 may at least temporarily store the uploaded contact tracing event records in an internal memory of the wireless access point 208 and/or may transmit the contact tracing event records to the data center 202, where the server 204 may cause the contact tracing event records to be stored in the data store 206. The wireless access point 208 returns to block 504 and continues connecting to in-range user devices 210, repeating blocks 504 through 508 repeatedly (e.g., until the end of a sailing, until the users leave the specified environment, etc.).

As uploaded records are stored in the data store 206, additional processing and/or organization may be performed. In one example, each uploaded record may be stored in the data store 206 in association with both the user of the first user device 210 that generated the record, and in association with the user of the second user device 210 that interacted with the first user device 210 to cause the record to be generated. In some embodiments, all contact tracing event records are retained. Alternatively, only the "close contact" records may be retained in association with the corresponding users. In another example, deduplication may be performed so as to remove duplicate records of the same contact tracing event (e.g., records generated by both user devices 210 in an event). As discussed above, deduplication of records can further include determining a final duration of the deduplicated event based on a union function of the two timestamp ranges of the records. Moreover, in some embodiments, the determination of which contact tracing event records are "close contacts" (e.g., decision state 416 of FIG. 4) may be performed by the processor 214 rather than at the user device 210 prior to upload.

At block 510, an index case may be identified. For example, in a cruise ship implementation, a user (e.g., a cruise ship guest or crewmember) may be identified as having a communicable disease. The disease may be detected during the sailing while the users are still within the ship, or may be detected subsequent to the sailing after the users have disembarked. In order to perform effective contact tracing for the period during with the index case user was aboard the ship, the contact tracing event records stored in the data store 206 may be used to identify the other users who were in close contact with the index case.

At block 512, a set of index case close contacts is determined. For example, the processor 204 may query the data store 206 to identify all of the close contact records stored in association with the index case user. Based on the identifiers of the other user devices 210 corresponding to each close contact record, the processor 204 may then generate a list of all other users who were involved in a "close contact" with the index case user. In some embodiments, the processor 204 may further determine any additional users (e.g., those additional users identified in close contact records with the index case close contacts subsequent to their close contact with the index case and/or after a predetermined incubation period) as secondary close contacts. At block 514, the list of "close contact" users, as well as any optional listing of secondary close contacts, is output, such as for notification and/or treatment of the close contacts and/or secondary close contacts.

Contact Tracing Based on Movement Profiles

As described above, a large number of location data points may be collected and stored for each user aboard a vessel. Accordingly, these location data points may advantageously be used in conjunction with an identified index case to identify others aboard the vessel that may have come into contact with a known pathogen.

In an example contact tracking implementation, one of the users (e.g., current or recent passengers or crew aboard a vessel, as described above) may be identified as an index case. In order to prevent further transmission of the pathogen, it may be desirable to identify a set of users that should be quarantined, for example, due to having been potentially in contact with the index case. It may similarly be desirable to identify a group of users who have not been in contact with the index case or with those who have been in contact with the index case, such that the non-exposed users may leave the vessel before possibly being exposed.

In some embodiments, when an index case is identified, an identification of the index case is provided to a server of an infectious disease tracking system on the vessel. The index case is preferably one of the many mobile device users aboard the vessel or previously aboard the vessel. The identification provided to the server may be, for example, a name, identification number, or other identifier uniquely corresponding to the individual user determined to be the index case.

In response to receiving the identification of the user determined to be the index case, the server can begin a contact tracing process to identify possible pathogen transmission paths. The server first determines a movement profile corresponding to the index case. In some embodiments, determining the movement profile may include collecting or obtaining from a data store all of the location data points associated with the index case. For example, the server may obtain from the data store all of the location data points that include an association with the index case user. In some cases the set of location data points associated with the index case may be ordered in a chronological order.

One or more additional movement profiles may further be determined. In some embodiments, the infectious disease tracking system may determine, based on the initial identification of the index case, that the vessel has an "infected" status, and may initiate the generation of movement profiles corresponding to all users aboard the vessel. In other embodiments, the infectious disease tracking system may generate movement profiles for only a subset of the users aboard the vessel, for example, to better utilize available computing resources. The subset may be determined, for example, by a "first-pass" method that selects users who may have come into contact with the index case, and only generates a full movement profile for each user in the subset.

In one example, the server determines a first set of contacts based on the location data points in the movement profile of the index case. The server may retrieve additional data stored by the wireless access points, and may identify, for each location data point in the index case movement profile, all of the additional location data points generated by the same wireless access point within a threshold time around the timestamp of the location data point (e.g., all location data points generated by the same wireless access point and having a timestamp within 10 seconds, 20 seconds, 30 seconds 1 minute, etc., of the index case location data point). The time threshold may be selected (e.g., by a medical officer or other crew member) based on specific transmission characteristics of the particular pathogen or disease. The time threshold can be selected based on guidance provided by public health officials. The server or other component of the system may generate a report or list including the names, identifying information, and/or other identifiers of all of these secondary users associated with any of the identified additional location data points. A movement profile may be generated for each secondary user in the list by the same process as described above for generating the movement profile for the index case.

In some embodiments, one or more additional close contacts (e.g., secondary users determined to have come into contact with the index case) may be determined based on other criteria outside of object tracking and location. For example, family members staying in the same stateroom as the index case, family members of the index case staying in different staterooms, and/or other travelers known to be acquainted with the index case based on having linked itineraries or reservations may be determined to be among the secondary users. Similarly, family members staying in the same stateroom as a secondary user, family members of a secondary user staying in different staterooms, and/or other travelers known to be acquainted with a secondary user based on having linked itineraries or reservations may be determined to be among the secondary users or tertiary users who have come into contact with secondary users.

In some embodiments, a similar comparison and time thresholding approach may further be implemented to identify the set of additional or tertiary users who may have come into contact with the secondary users. This additional identification may be desirable as it allows for the identification of those users who have not been in close contact with the index case but who may have been exposed to the pathogen by coming into contact with a secondary user who did contact the index case.

When the set of secondary and/or tertiary users has been determined, the infectious disease tracking system may generate one or more lists such as a quarantine list (e.g., including the index case, the secondary users who are determined to have potentially come into close contact with the index case, and optionally the tertiary users who are determined to have potentially come into close contact with the secondary users) and/or a list of non-exposed users who may be allowed to leave the vessel (e.g., including all passengers and crew who are determined not to have come into contact with the index case and/or with any of the secondary users).

In some embodiments, the system may take one or more additional actions in addition to generating the lists of exposed and non-exposed users as described above. For example, in some embodiments the system may further be configured to identify surfaces located along or near the movement profile of an index case or of a secondary user, such that a cleaning crew can quickly be dispatched to disinfect those areas. For example, if a movement profile indicates that a passenger, after being exposed to a pathogen, visited a restaurant, bar, swimming pool, lounge area, or other area where the passenger may have stopped and touched one or more surfaces, those areas may be identified based on the passenger's movement profile and cleaned thoroughly to avoid transmission of the pathogen to others. In some embodiments, exact surfaces touched by an index case or by secondary users may be pinpointed, for example, based on video or still images obtained from a CCTV or other imaging system that monitors the areas identified within the movement profile. Accordingly, the systems and methods of the present technology can advantageously mitigate transmission both by person-to-person contact and by secondary surface transmission.

Implementations of the present disclosure can advantageously perform contact tracing for guests currently embarked on a voyage even in situations where the index case is identified after the index case has disembarked. The infectious disease tracking system can retain location data points associated with a particular voyage in the data store for a predetermined retention period. The predetermined retention period can be temporal (for example, a period of two weeks or one month) or voyage-based (for example, for the duration of the next voyage or the duration of the next two voyages). In one non-limiting example, a cruise operator may learn during Voyage B of Ship X that a guest embarked on an immediately preceding voyage, Voyage A, of Ship X is an index case. In implementations of the present disclosure, contact tracing can be performed for all guests and crewmembers that were embarked on Ship X during Voyage A (using location data points stored in the data store during Voyage A and retained in the data store for the predetermined retention period), and for all guests and crewmembers that are currently embarked on Ship X during Voyage B (using location data points stored in the data store during Voyage B). Accordingly, embodiments of the present disclosure can perform backward-looking contact tracing to identify individuals that came in close contact with an index case during a prior voyage. This is particularly advantageous in situations where the individual that came in close contact with an index case during a prior voyage did not debark the ship at the end of the prior voyage. Returning to the prior example, an individual who came in close contact with an index case during Voyage A may not have debarked Ship X at the end of Voyage A, but continued her stay on Ship X during Voyage B. If this individual contracted the disease during Voyage A from the index case, the individual may be actively transmitting the infectious disease to guests embarked on Ship X during Voyage B, depending on the incubation period of the disease and other factors. Rapid and accurate contract tracing across multiple voyages is particularly advantageous in cases of a novel disease with an uncertain or unknown incubation period.

Further Example Embodiments

1. An infectious disease tracking system for a cruise ship, the system comprising:
   a plurality of wireless access points disposed within the cruise ship, each wireless access point of the plurality of wireless access points comprising:
      a communication module configured to detect and identify mobile devices in proximity to the wireless access point; and
      a processor in communication with the communication module, the processor configured to cause storage, in a data store, of a location data point each time a mobile device is detected, each location data point comprising:
         a timestamp;
         an association with the wireless access point; and
         an association with a user corresponding to the mobile device; and
   a server in communication with the data store, the server configured to:
      receive an identification of a first user determined to be an index case of a disease;
      determine, based on the timestamps and the wireless access points corresponding to a plurality of location data points associated with the first user, a movement profile corresponding to the first user;
      identify, based on the movement profile, one or more additional location data points indicative of a possible contact with the first user, each of the one or more additional location data points associated with a user other than the first user; and
      determine, based on the one or more additional location data points, a set of second users who may have come into contact with the first user.

2. The infectious disease tracking system of Embodiment 1, wherein the server is further configured to determine movement profiles corresponding to the second users.

3. The infectious disease tracking system of Embodiment 2, wherein the server is further configured to determine, based at least in part on the movement profiles corresponding to the second users, a set of third users who may have come into contact with one or more of the second users.

4. The infectious disease tracking system of Embodiment 3, wherein the server is further configured to generate, based at least in part on the set of second users, the set of third users, and a passenger manifest of the cruise ship, a list of passengers who have not come into contact with the first user or the one or more other users who have come into contact with the first user.

5. The infectious disease tracking system of Embodiment 3, wherein the server is further configured to generate, based at least in part on the set of second users and the set of third users, a list of passengers to be quarantined.

6. The infectious disease tracking system of Embodiment 1, wherein each of the mobile devices comprises one or more of a personal computing device or a wearable electronic device.

7. The infectious disease tracking system of Embodiment 1, wherein the communication module of each wireless access point is configured to detect and identify mobile devices using one or more of near Bluetooth, Bluetooth Low Energy (BLE), near-field communication (NFC), Wi-Fi, radio-frequency identification (RFID), or a wireless broadband communication protocol.

8. The infectious disease tracking system of Embodiment 1, wherein each of the one or more additional location data points is identified if the additional location data point is associated with the same wireless access point and has a timestamp within a threshold time relative to at least one of the location data points associated with the first user.

9. The infectious disease tracking system of Embodiment 1, wherein the server is further in communication with an imaging system that records images or video of areas of the cruise ship where the wireless access points are located.

10. The infectious disease tracking system of Embodiment 9, wherein the server is further configured to:
obtain, from the imaging system, an image or video file corresponding to each of the additional location data points; and
store an association between each image or video file and the second user associated with the corresponding additional location data point.

11. The infectious disease tracking system of Embodiment 9, wherein the imaging system is further configured to determine facial recognition results based on images captured by the imaging system, wherein the infection control system is further configured to identify second users based on the facial recognition results.

12. The infectious disease tracking system of Embodiment 1, wherein the system retains the location data points in the data store for a predetermined retention period.

13. The infectious disease tracking system of Embodiment 12, wherein the predetermined retention period is one month.

14. The infectious disease tracking system of Embodiment 12, wherein the system retains the location data points stored in the data store during a first voyage of the cruise ship until at least the end of a subsequent voyage of the cruise ship.

What is claimed is:

1. An infectious disease tracking system for a cruise ship, the system comprising:
a plurality of user devices, each user device comprising a wireless communication module, one or more processors, and memory storing computer-executable instructions that, when executed by the one or more processors, cause the one or more processors to at least:
detect, using the wireless communication module, a signal emitted by another one of the plurality of user devices;
determine that a strength of the signal exceeds a predetermined event initiation signal strength threshold;
store, in the memory, a contact tracing event record by initiating periodic recording of contract tracing event data points associated with a first contact tracing event between the user device and the other one of the plurality of user devices in response to determining that the strength of the signal exceeds the predetermined event initiation signal strength threshold; and
transmit the contact tracing event record.

2. The infectious disease tracking system of claim 1, wherein storing the contact tracing event record comprises:
storing an initial contact tracing event data point including at least a timestamp and an identifier of the other one of the plurality of user devices;
updating the contact tracing event record by storing additional contact tracing event data points based on subsequent signals received from the other one of the plurality of user devices; and
terminating storage of additional contact tracing event data points.

3. The infectious disease tracking system of claim 2, wherein the instructions further cause the one or more processors to compare strengths of the subsequent signals to an event interruption signal strength threshold, and wherein the storage of additional contact tracing event data points is terminated based at least in part on at least one of the subsequent signals having a strength below the event interruption signal strength threshold.

4. The infectious disease tracking system of claim 3, wherein the storage of additional contact tracing event data points is terminated based on the strengths of the subsequent signals remaining below the event interruption signal strength threshold for at least a predetermined grace period.

5. The infectious disease tracking system of claim 4, wherein the grace period is 90 seconds.

6. The infectious disease tracking system of claim 3, wherein the instructions further cause the one or more processors to at least:
suspend the storage of additional contact tracing event data points based on a first one of the subsequent signals having a strength below the event interruption signal strength threshold; and
resume the storage of additional contact tracing event data points in response to detecting a second one of the subsequent signals having a strength above the event interruption signal strength threshold prior to the expiration of a predetermined grace period.

7. The infectious disease tracking system of claim 3, wherein the event interruption signal strength threshold is lower than the event initiation signal strength threshold.

8. The infectious disease tracking system of claim 7, wherein the event initiation signal strength threshold is a Received Signal Strength Indicator value of −68 decibel-milliwatts (dBm), and wherein the event interruption signal strength threshold is lower than −68 dBm.

9. The infectious disease tracking system of claim 1, wherein the event initiation signal strength threshold comprises a predetermined Received Signal Strength Indicator (RSSI) value.

10. The infectious disease tracking system of claim 9, wherein the contact tracing event record comprises a plurality of contact tracing event data points, each contact tracing event data point comprising at least a timestamp and an RSSI value.

11. The infectious disease tracking system of claim 9, wherein the event initiation signal strength threshold is −68 decibel-milliwatts (dBm).

12. The infectious disease tracking system of claim 1, wherein the contact tracing event record indicates at least a duration of the first contact tracing event and an identifier of the other one of the plurality of user devices or of a user thereof.

13. The infectious disease tracking system of claim 12, wherein the instructions further cause the one or more processors to modify the contact tracing event record to indicate a close contact based on the duration exceeding a predetermined close contact time threshold.

14. The infectious disease tracking system of claim 12, wherein the close contact time threshold is one of 5 minutes or 15 minutes.

15. The infectious disease tracking system of claim 1, wherein the wireless communication module of each user device is configured to communicate with the wireless communication modules of the other user devices using Bluetooth Low Energy (BLE) protocol.

16. The infectious disease tracking system of claim 1, further comprising a plurality of wireless access points disposed within the cruise ship and configured to receive the transmitted contact tracing event record.

17. The infectious disease tracking system of claim 16, wherein the plurality of wireless access points are configured to communicate with each of the user devices using Bluetooth Low Energy (BLE) protocol.

18. The infectious disease tracking system of claim 16, wherein the instructions cause the one or more processors to store a plurality of contact tracing event records and to transmit a set of most recent contact tracing event records to an individual wireless access point of the plurality of wireless access points in response to detecting the individual wireless access point.

19. The infectious disease tracking system of claim 16, wherein each of the plurality of wireless access points is in communication with a server and configured to transmit the received contact tracing event records to the server.

20. The infectious disease tracking system of claim 19, wherein the server is configured to store each contact tracing event record in a data store in association with an identifier of the user device that generated the contact tracing event record or of a user thereof.

21. The infectious disease tracking system of claim 20, wherein the server is further configured to store, in the data store, an association between each contact tracing event record and an identifier of a second user device identified in the contact tracing event record or of a user thereof.

22. The infectious disease tracking system of claim 21, wherein the server is further configured to identify pairs of contact tracing event records generated by different user devices corresponding to a same contact tracing event, based at least in part on timestamps included within the pairs of contact tracing event records.

23. The infectious disease tracking system of claim 22, wherein the server is further configured to perform deduplication based on the identified pairs of contact tracing event records.

24. The infectious disease tracking system of claim 20, wherein the server is further configured at least:
  receive an identification of a user identified as an index case user of an infectious disease;
  query the data store, in response to the identification of the user, to determine a set of close contact users having close contact records associated with the index case user; and
  output a contact tracing result identifying the set of close contact users.

25. The infectious disease tracking system of claim 1, further comprising:
  a server; and
  a plurality of wireless access points disposed within the cruise ship, each wireless access point configured to wirelessly receive the contact tracing event records from the user devices and to transmit the received contact tracing event records to the server;
  wherein the server is further configured to at least:
    store the contact tracing event records in a data store;
    receive an identification of a user identified as an index case user of an infectious disease;
    query the data store, in response to the identification of the user, to determine a set of close contact users having close contact records associated with the index case user; and
    output a contact tracing result identifying the set of close contact users.

* * * * *